(12) United States Patent
Lie

(10) Patent No.: US 11,141,311 B2
(45) Date of Patent: Oct. 12, 2021

(54) APPARATUS FOR ADJUSTING TEMPERATURE OF BODY

(71) Applicant: Claus Lie, Aabybro (DK)

(72) Inventor: Claus Lie, Aabybro (DK)

(*) Notice: Subject to any disclaimer, the term of this patent is extended or adjusted under 35 U.S.C. 154(b) by 0 days.

(21) Appl. No.: 16/097,080

(22) PCT Filed: Apr. 28, 2017

(86) PCT No.: PCT/DK2017/050130
§ 371 (c)(1),
(2) Date: Oct. 26, 2018

(87) PCT Pub. No.: WO2017/186249
PCT Pub. Date: Nov. 2, 2017

(65) Prior Publication Data
US 2019/0105193 A1    Apr. 11, 2019

(30) Foreign Application Priority Data
Apr. 28, 2016    (DK) .......................... PA 2016 70265

(51) Int. Cl.
*A61F 7/12* (2006.01)
*A61B 17/34* (2006.01)

(52) U.S. Cl.
CPC ............ *A61F 7/12* (2013.01); *A61B 17/3415* (2013.01); *A61F 7/123* (2013.01); *A61B 17/3421* (2013.01); *A61B 17/3462* (2013.01); *A61B 2017/3437* (2013.01); *A61B 2017/3492* (2013.01); *A61F 2007/126* (2013.01)

(58) Field of Classification Search
CPC ...... A61F 7/12; A61F 7/123; A61F 2007/126; A61F 2007/0022; A61B 17/3415; A61B 17/3421; A61B 17/3423; A61B 17/3462; A61B 2017/3437
See application file for complete search history.

(56) References Cited

U.S. PATENT DOCUMENTS 5,720,773 A    2/1998 Lopez-Claros
5,799,661 A    9/1998 Boyd et al.
(Continued)

FOREIGN PATENT DOCUMENTS

CN    1190340 A    8/1998
CN    102058931 A    5/2011
(Continued)

OTHER PUBLICATIONS

JP 10-262983 (Fuji Photo Optical CO) Translated by Espacenet Mar. 27, 1997 [Retreived on Aug. 7, 2019] (Year: 1997).*
(Continued)

*Primary Examiner* — Eun H Wa Kim
*Assistant Examiner* — Adam Z Minchella
(74) *Attorney, Agent, or Firm* — Mollborn Patents, Inc.; Fredrik Mollborn

(57) ABSTRACT

The invention discloses an apparatus for adjusting the temperature of a body comprising a sheath for providing a channel from outside said body to a cavity inside said body, where said sheath comprises a guiding section being angular to said channel. The apparatus further comprises a heat exchange unit comprising an inlet and an outlet, an outer contour and an inner fluid channel, adapted for inserting through said channel of said sheath.

10 Claims, 8 Drawing Sheets

(56) References Cited

U.S. PATENT DOCUMENTS

| | | | |
|---|---|---|---|
| 6,652,565 B1* | 11/2003 | Shimada | A61B 17/3415 607/104 |
| 6,733,517 B1 | 5/2004 | Collins | |
| 2003/0088212 A1 | 5/2003 | Tal | |
| 2003/0097082 A1* | 5/2003 | Purdy | A61B 17/12136 600/594 |
| 2008/0008987 A1* | 1/2008 | Bianco | A01N 1/02 435/1.2 |
| 2009/0182288 A1* | 7/2009 | Spenciner | A61B 17/3431 604/264 |
| 2010/0030145 A1 | 2/2010 | Ghodsian et al. | |
| 2010/0256453 A1* | 10/2010 | Hammond | A61B 17/3462 600/210 |
| 2012/0289757 A1 | 11/2012 | Boyden et al. | |
| 2018/0207028 A1* | 7/2018 | Hu | A61F 7/0085 |

FOREIGN PATENT DOCUMENTS

| | | | |
|---|---|---|---|
| EP | 2238928 A1 | | 10/2010 |
| JP | 10262983 A | * | 10/1998 |
| JP | H10262983 A | | 10/1998 |
| JP | 2002500915 A | | 1/2002 |
| JP | 2010207619 A | | 9/2010 |
| WO | 0112061 A1 | | 2/2001 |
| WO | 03086253 A2 | | 10/2003 |
| WO | 2004034940 A1 | | 4/2004 |
| WO | 2004060465 A3 | | 7/2004 |
| WO | 2016014748 A1 | | 1/2016 |

OTHER PUBLICATIONS

International Preliminary Report on Patentability; International application No. PCT/DK2017/050130; International Preliminary Examining Authority; Date of completion of this report Aug. 7, 2018; pp. 1-6.

PCT Written Opinion of the International Searching Authority; International application No. PCT/DK2017/050130; International Searching Authority; pp. 1-5.

Written Opinion of the International Preliminary Examining Authority; International application No. PCT/DK2017/050130; International Preliminary Examining Authority; dated Mar. 27, 2018; pp. 1-5.

Danish Office Action, Second technical examination ; Application No. PA 2016 70265; Notification Date: Apr. 9, 2018.

Danish Office Action, Intention to grant; Application No. PA 2016 70265; Notification Date: Jul. 1, 2018.

\* cited by examiner

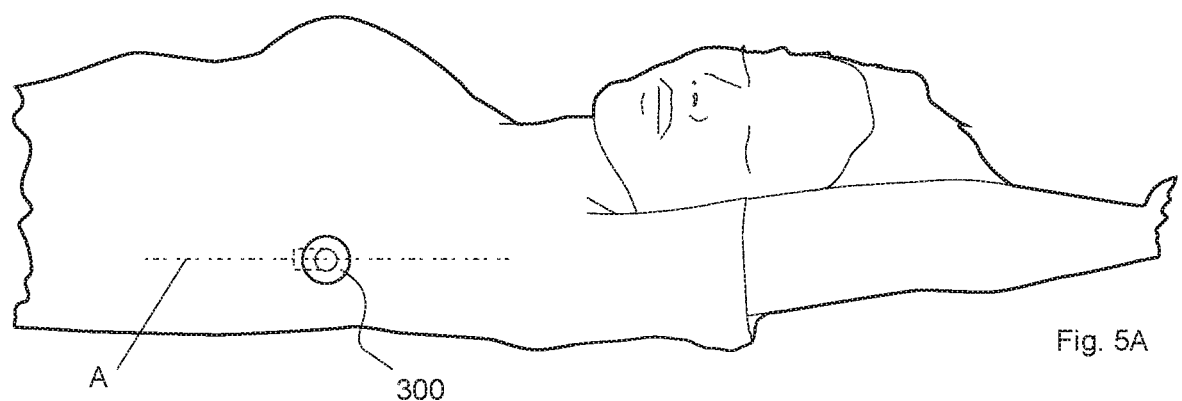
Fig. 5A
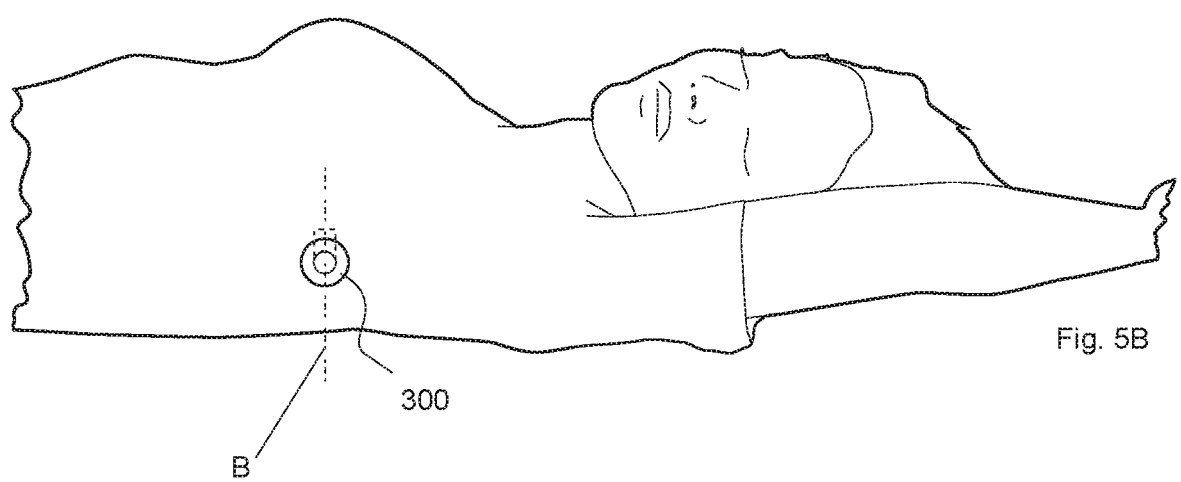
Fig. 5B
Fig. 5

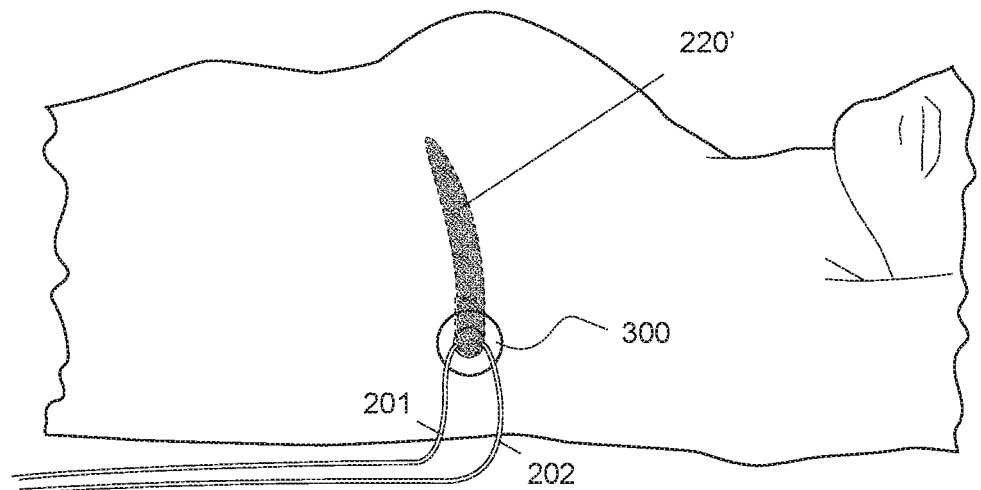
Fig. 6A
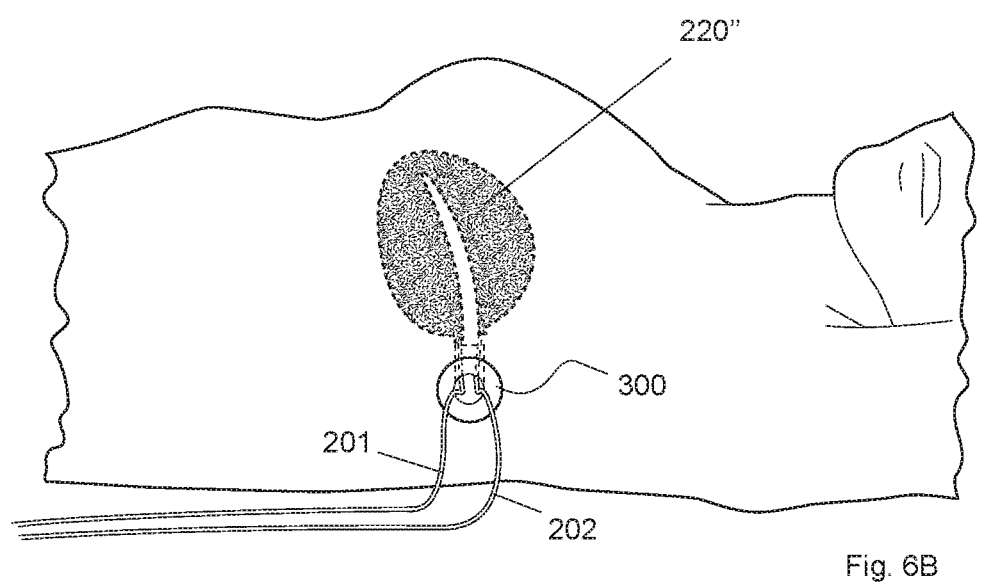
Fig. 6B
Fig. 6

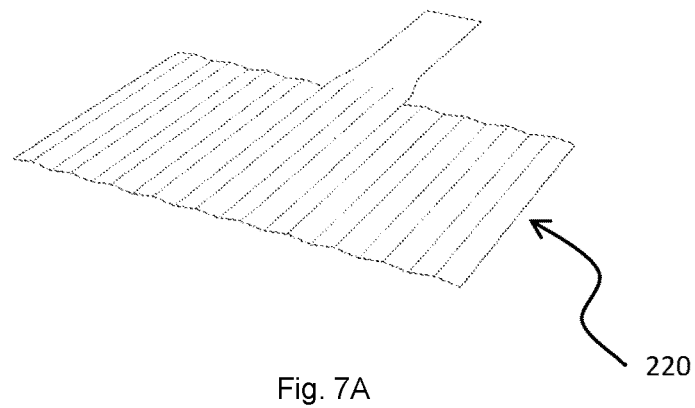
Fig. 7A
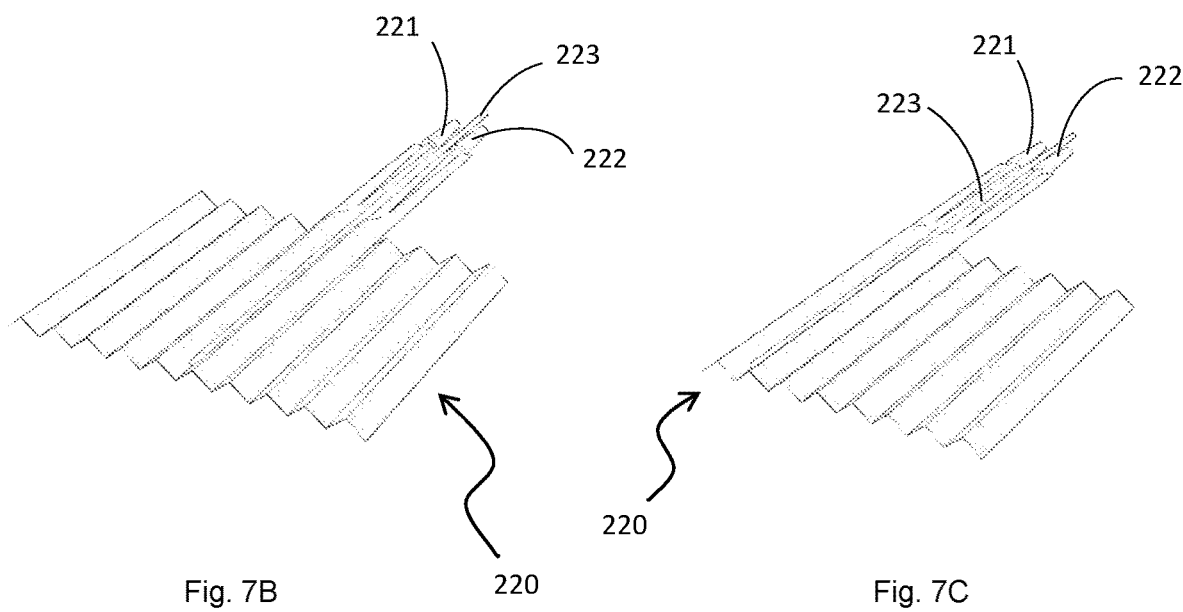
Fig. 7B
Fig. 7C

APPARATUS FOR ADJUSTING TEMPERATURE OF BODY

FIELD OF THE INVENTION

An apparatus for adjusting the temperature of a body and components for such an apparatus.

DESCRIPTION OF PRIOR ART

Controlling the temperature of bodies of patients is sometimes a preferable or important part of medical treatment. This is for example the case for people who have been cooled down to a point, where it has become dangerous to their health, such as especially those suffering from hypothermia. These patients may die if not treated correctly, and even severe interventions are often performed to try to help the body recover.

Most simply, the body may be heated or cooled by outside elements, for example blankets, warm water and so on.

A more severe intervention is extracorporeal heating, where blood is drawn from the patient and warmed actively by an outside heater, whereupon the blood is reintroduced into the body. This has the advantage of having a higher heat transfer speed compared to simple heating by blankets etc.

Further, WO2006/036357A2 discloses a system for controlling the temperature of a patient by way of an intravenous heat control system, where a catheter is placed within the veins of a patient, and where controlling the temperature of a liquid within the catheter then controls the temperature of the blood of the patient, thus either cooling or heating the patient. This has the advantage of not drawing blood out of the body of the patient, thus likely inducing less strain this way.

US2002/151942A1, US2004/044387, WO0158397A1 and U.S. Pat. No. 6,685,733B1 disclose variations of intravenous temperature controlling apparatuses with different placements within the bloodstream and different shapes of the catheters within the blood stream. These all seek to increase the efficiency of intravenous heat controlling.

WO01/12061A1 discloses a catheter for insertion into a blood vessel, i.e. an intravenous temperature controlling apparatus. Said catheter comprises an inlet and outlets for a coolant and further comprises expandable balloons. Further, the catheter is adapted for inserting through a sheath. The catheter may be connected to a cooling system through a coolant supply line and a coolant return line.

WO2004/060465 discloses a catheter useful in navigating and performing procedures in the subarachnoid space. Thus, it is understood, that said catheter is designed to enter blood vessels. In an embodiment of the invention, the catheter comprises, in a distal end, a heat exchanging element which is supplied by a liquid through an inlet and an outlet. The liquid may pass by a heat exchanger. Thus, the document may be considered an intravenous temperature controlling apparatus.

EP2238928A1 discloses a surgical access portal, i.e. relates to a sheath, comprising a seal housing and a sleeve mounted to the sleeve housing having an internal longitudinal passage adapted to provide access to underlying tissue. A sponge is disposed distally of the seal and absorbs fluids that enter the seal housing.

US2009/182288A1 discloses a cannula, i.e. relates to a sheath, which may be flexible to collapse completely in the tissue and still allow instruments to pass through the portal.

JPH10262983 discloses a trocar, i.e. relates to a sheath, for use in surgical procedures, whereby access to an underlying tissue is provided through an opening in an overlying tissue. The trocar comprises a manipulating part and an inserting part, where said inserting part comprises a rigid pipe part and an angle (bendable) part composed of movable links. The bendable part may bend once inside the underlying tissue, whereby instruments operated through the trocar may be directed in different directions inside said underlying tissue.

U.S. Pat. No. 6,733,517B1 discloses an introducer sheath and a catheter designed to enter a patient's vena cava system, i.e. a blood vessel. Thus, the document relates to an intravenous temperature controlling apparatus. The sheath is specifically designed to position the catheter in the correct position prior to use of said catheter. The catheter at least comprises heat exchange elements. The catheter is a substantially elongate structure of a generally cylindrical shape adapted for insertion into the body. It is explicitly stated that considerations in selecting the appropriate material of the catheter include resistance to buckling. The heat exchange elements are arranged as fluid-carrying inflatable balloons being radially disposed around the width of the catheter. In a preferred embodiment, the balloon diameter is 4 mm-10 mm. A first lumen serves as an inflow channel supplying the balloon with heat exchange fluid which is circulated through the catheter, while a second lumen serves as an outflow channel.

Alternatively, heated or cooled liquid may be injected directly into cavities inside the patient. For example, to treat hypothermia a heated liquid is injected into the pleural cavity or the abdominal cavity. This has the advantage of heating centrally in the body, where the heating is most critical.

For the simple heating, heat transfer is not sufficient to help in many cases. Extracorporeal heating, although it is faster than simple heating, is still not quite fast enough for all situations due to the blood being typically removed from a vein distant to the heart, where heat transfer is then not achieved centrally.

Intravenous heat controlling, whether it is heating or cooling, requires insertion of foreign elements into the blood stream of a patient. To achieve the best results relating to heat transfer, the catheters should be inserted as close to the heart as possible, thus requiring advanced surgery. Further and complicated even more, when these systems are introduced close to the heart, their design aspires to a maximal surface area to increase heat transfer which necessarily requires a significant size. Blood flow is then necessarily hampered which may create further complications relating to blood clotting, or more accurately, thrombosis. Anticoagulant medicine is then needed if intravenous heating is utilised, thus bringing the complications which these entail.

Directly injecting heated or cooled liquid into cavities of a patient to control his/her temperature necessarily builds up liquid in the patient which must be drained. The liquid used has been in direct contact with the patient and is therefore not safe for further use. Treatment by this method may use as much as a hundred litres of medical grade isotonic saline. Besides the high use of liquid, the electrolyte balance may be disrupted, whereby salt is washed out with the saline. Lastly, heating is performed most preferably in the pleural cavity as it is closest to the heart and lungs of the two cavities. However, injecting liquid into the pleural cavity removes the vacuum needed to retain the function of the lungs consequently puncturing the lungs.

Further, the above-described methods all require significant amounts of equipment, whereby treatment of patients is limited to hospitals. This is a problem as treatment of rescued persons cannot begin either in a helicopter or in an ambulance, whereby treatment may be delayed for a long period of time. Further, the specialised personnel needed for the heart-related surgery may not be available for use in response teams.

SUMMARY OF THE INVENTION

The invention discloses a system and an apparatus for adjusting the temperature of a body comprising a sheath for providing a channel from outside said body to a cavity inside said body, where said sheath comprises a guiding section being angular to said channel and a heat exchange unit comprising an inner fluid channel, an outer contour, a fluid inlet, and a fluid outlet, where said inner fluid channel of said heat exchange unit comprises a series of channels between said fluid inlet and said fluid outlet, where said heat exchange unit is adapted for inserting through the channel of said sheath and into the cavity inside said body in a compressed state, and where liquid entering the fluid inlet and into the heat exchange unit expands the series of channels and eventually expands the heat exchange unit fully, thus enabling liquid to pass through said fluid inlet, into said series of channels and from said series of channels through said fluid outlet.

By this system, a more benign operation may be performed on a patient, whereby severe trauma is hopefully avoided while supplying an effective and rapid temperature adjustment.

By body is meant a body of an animal, preferably a mammal, most preferably a human. By cavity is meant an inner compartment of the body able to receive a heat exchange unit as described. Preferably, a pleural cavity or an abdominal cavity is meant. In an embodiment of the invention, blood vessels are thereby expressly understood to not be encompassed.

In an embodiment of the invention, the sheath further comprises fastening means for securing said sheath to skin around said sheath. Thereby, once the correct orientation of the guiding means is established, it can be maintained conveniently while also avoiding depressurisation of the cavity of the patient.

In an embodiment of the invention, the heat exchange unit is inserted into either the right pleural cavity, the left pleural cavity, the abdominal cavity, or a combination of any of the cavities. Thereby, access is gained to a central region of the body without penetrating blood vessels.

In an embodiment of the invention, the sheath further comprises a self-sealing means inside said channel. Thereby, depressurisation of the cavity of the patient is avoided, while also allowing the operation procedure to be performed stepwise and be interrupted after insertion of the sheath without harm to the patient.

In an embodiment of the invention, the heat exchange unit is adapted to change shape, where emptying said inner channel of said heat exchange unit of fluid, a compressed shape is achieved, and where an outer contour of said heat exchange unit is smaller than the inner diameter of said channel of said sheath.

Thereby, a heat exchange unit may be inserted into the cavity having a larger surface area than would otherwise be possible through a hole of the same size.

In an embodiment of the invention, at least two heat exchange units may be inserted into at least one cavity of the patient, such as for example inserting a heat exchange unit into each pleural cavity, inserting one into the pleural cavity and one into the abdominal cavity, or even several into each.

This allows conveniently placing heat exchange units centrally. By this, a fast and central heating of the patient is achieved.

The invention further relates to a sheath and a heat exchange unit for use in a system according to the invention.

In an embodiment of the invention, it further relates to a treatment controlling means and an inlet tube and an outlet tube to be used as part of a system according to the invention.

LIST OF FIGURES

In the following, example embodiments are described according to the invention.

FIG. 1 is a side view of a patient and an advantageous insertion region.

FIG. 2 is a view of a liquid heat controlling system according to the invention.

FIG. 3 is a cross-sectional view of a sheath according to the invention.

FIG. 4 illustrates a pleural heating apparatus according to the invention.

FIG. 5 illustrates the sheath inserted into a patient according to the invention.

FIG. 6 illustrates a heat transfer unit inserted into a patient according to the invention.

FIGS. 7A-7C illustrates a heat transfer unit in various stages of folding, according to the invention.

FIG. 8 shows a sequential unfolding of a heat exchange unit from a compressed state to an expanded state, according to the invention.

The heat exchange unit 220 and the treatment controller 210 are connected through an inlet tube 201 and outlet tube 202. The inlet tube connects the treatment controller to the inlet on the heat exchange unit. Liquid having substantially the target temperature flows through the inlet tube. The outlet tube connects the heat exchange unit to the temperature adjuster, and the liquid flowing through the outlet tube has substantially the temperature of the body. This ensures a closed liquid loop which allows a limited compression of the lungs as consequence of heating compared to injecting liquid directly into the pleural cavity as well as a significantly controlled and lower liquid use compared to free liquid flow into a cavity.

Figure 1:
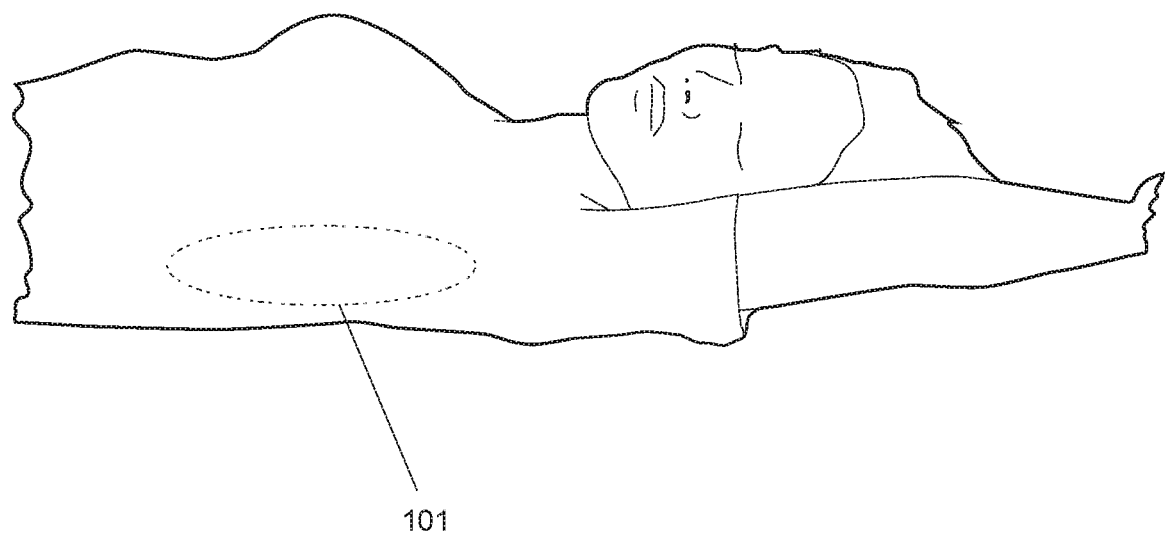
In FIG. 1, a preferable insertion location of a patient is seen. Any location on the body may be used, where insertion below the armpit may be a useful location for achieving a non-traumatising access into the pleural cavity. A cut is made, for example between two ribs. Access to the pleural cavity is conveniently achieved by making a cut of 1.5 cm-2 cm in breadth, although there is no technical limitation as to the size of the cut.
Figure 2:
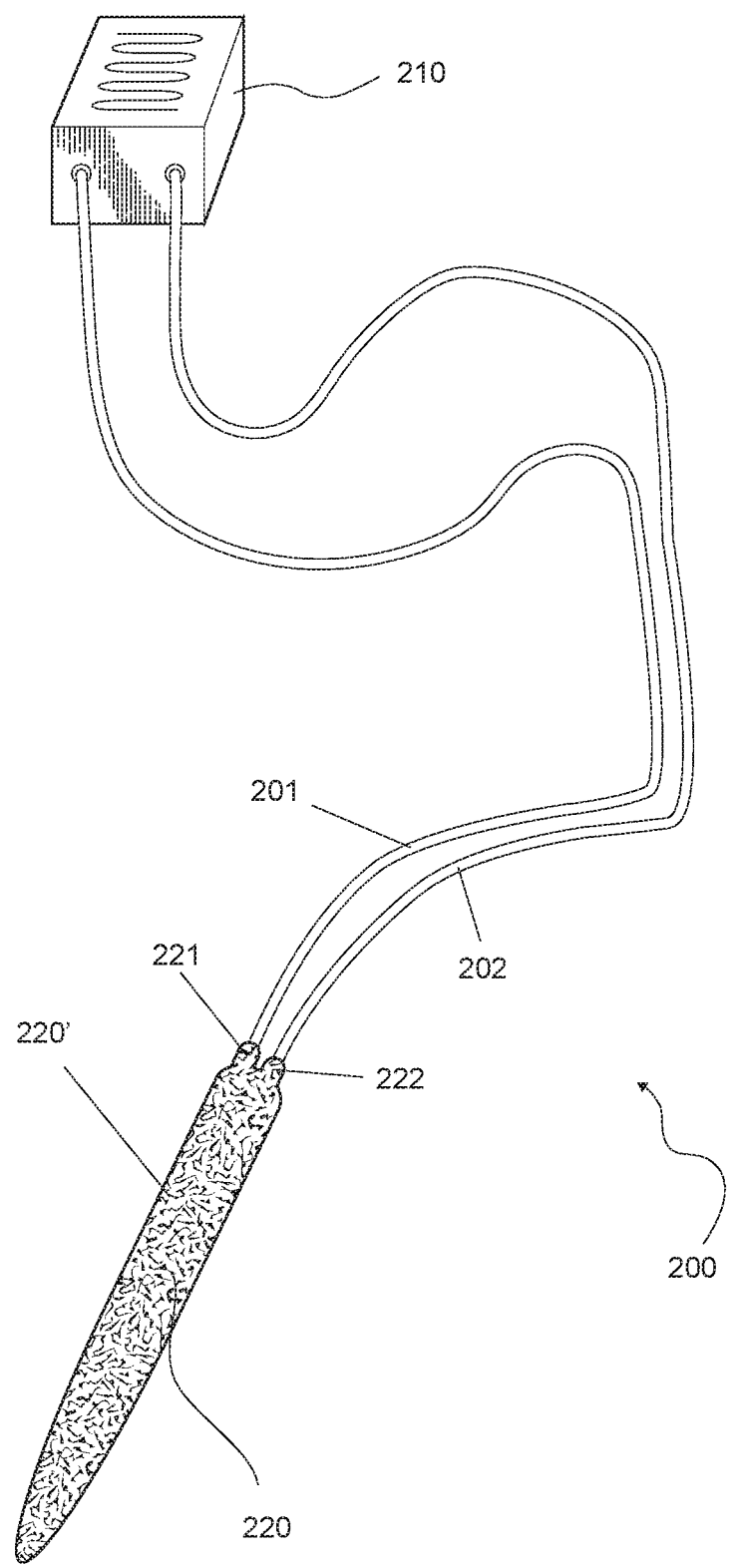
FIG. 2 illustrates a liquid heat transfer system 200 according to the invention. This liquid heat transfer system 200 comprises a heat exchange unit 220 for absorbing heat from the body or radiating heat to the body, a treatment controller unit 210 for warming or cooling a heat adjustment liquid, an inlet tube 201 and an outlet tube 202 for transporting the heat adjustment liquid between the treatment controller unit to and the heat exchange unit.

The heat exchange unit 220 is illustrated in FIG. 2 as a compressed heat exchange unit 220'. In this state, the heat exchange unit is emptied of fluid, thus being prepared for insertion into the patient. The heat exchange unit is a channel through which liquid flows to transfer heat between the liquid and the body.

The heat exchange unit is formed of a flexible material which allows it to be compressed before insertion into the body and then being expandable after insertion. This compression may be performed in a variety of ways, where bending it in a wave-like fashion may be advantageous to allow easy expansion by introduction of liquid in its inner channel after insertion. It may, however, also be rolled or compressed in a different manner, such as randomly. The heat exchange unit is compressed either before connection to the liquid system 200, such as at time of production, or it is compressed by the treatment controller. In an embodiment of the invention, the heat exchange unit compresses automatically to a substantially cylindrical shape or to have an elliptical cross section. In this state, the outer diameter of the heat exchange unit is smaller than the inner diameter of the sheath, and it may thus be inserted through the sheath 300. In another embodiment of the invention, the compression of the heat exchange unit 220 is enhanced by inserting it into a tube having a fitting diameter during compression, where a fitting diameter may be a diameter equal to the diameter of the sheath.

The heat exchange unit 220 is produced in a flexible medical grade material, such as silicone, polyurethane, polyethylene, polytetrafluoroethylene or another material, typically a polymer and has at least two openings being an inlet 221 and an outlet 222.

The treatment controller unit 210 is adapted to heat or cool a liquid passing through it. This may be achieved through heating elements or cooling elements. In one embodiment of the invention, the temperature controller unit heats or cools the liquid to a predetermined value. In another embodiment, the target value may be changed. This is especially useful as different conditions may require different target temperatures. Also, this allows faster action by initially heating or cooling the liquid at a high rate.

In an embodiment of the invention, where the target temperature may be changed, the treatment controller 210 comprises both heating and cooling elements.

In an embodiment of the invention, the heat transfer system further comprises a sensing unit measuring parameters relating to the heat transfer liquid. These parameters comprise at least one of either the liquid pressure or liquid temperature. For example, liquid pressure may be monitored in either of or both the tubes 201, 202. Temperature may be monitored in either tube 201, 202 and/or in the heat exchange unit. Measuring the temperature in the outlet tube allows evaluating the transferred heat to or from the liquid which informs on treatment.

In another embodiment of the invention, temperature is monitored at the inlet tube, at the outlet tube and at a position corresponding to the heat exchange unit, whereby heat transfer to the patient may be precisely calculated compensating for any loss happening between the inlet tube and outlet tube inside the sheath.

Figure 3:
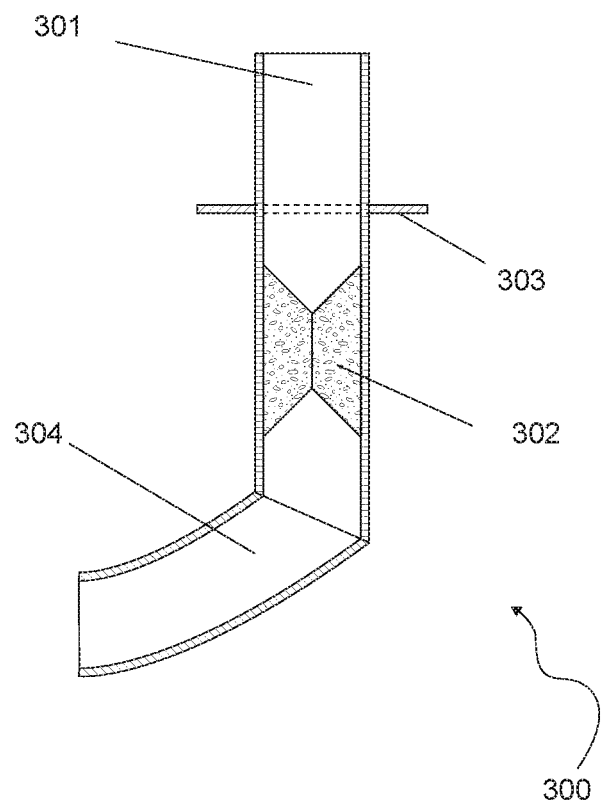

FIG. 3 is a cross-sectional view of a sheath 300 according to the invention said sheath 300 being adapted to allow convenient access to a desired cavity of a patient for placing the heat transfer unit. The sheath 300 comprises: a channel 301 for inserting the compressed heat exchange unit 220' through, a self-sealing means 302 inside said channel 301 for inhibiting depressurisation of the cavity through the channel before, during and/or ideally after use, a fastening means 303 for fastening the sheath to the body and inhibiting depressurisation and bleeding around the sheath, and a guiding section 304 for directing the inserted sheath in a desired direction once inside the desired cavity, preferably the pleural cavity.

The channel 301 may have various shapes, such as having a substantially hard cylindrical shape which allows the hole to stay expanded. In another embodiment, the sheath is made substantially of a softer material, but comprises at least two elongated elements of a stiffer material, such as metal wire or hard plastic sheets or tubes embedded into the wall of the channel along its length, whereby the sheath can be rotated and controlled even inside the body. In this embodiment, the sheath does not automatically retain its cylindrical shape against the pressure exerted by the body, instead substantially allowing the hole to close thus avoiding depressurisation of the pleural cavity.

Preferably, the inner channel through the sheath comprises a self-sealing means 302. This is desirable so as to inhibit depressurisation of the pleural cavity through the channel 301 of the sheath 300 as well as limiting or avoiding fluid communication, thus potentially avoiding contaminants. By self-sealing is meant a structure that allows the sheath to at least inhibit fluid communication between the cavity of the patient and the outside while inserted in the patient. The self-sealing means does not have to be repeatedly sealable, and may thus be a film that is breakable on further treatment. In a preferable embodiment of the invention, the self-sealing means seals around the heat exchange unit on insertion and later seals around the tubes, while also allowing the pulling out of the heat exchange unit without the heat exchange unit getting stuck.

In an embodiment of the invention, this self-sealing means is formed by the channel 301 being flexible with at least two stiffening elements in the length of the sheath. In this embodiment, the flexible wall of the sheath allows the walls of the sheath to be pressed towards each other under the forces of the body and so seals the sheath at least partially.

In an embodiment of the invention, a channel 301 is fitted with a self-sealing membrane. In another embodiment of the invention, a sealing section is fitted with a compressible and at least partially air-impregnable material such as a closed-cell or an open-cell foam material adhered along the inside radial wall of the channel. This material limits depressurisation of the cavity substantially while allowing the heat exchange unit to press it outwards towards the inner wall of the channel on insertion of the heat exchange unit. In an embodiment of the invention, the self-sealing function is achieved by a combination of a flexible channel and a layer of compressible and at least partially air-impregnable material inside the channel 301.

The sheath is fastened to the body of the patient during treatment by fastening means 303. Conveniently, this is an adhesive fitted to adhere to the body of the patient further providing fluid tight seal around the sheath. This further ensures that the pleural cavity is not depressurised as a result of access to the pleural cavity between the hole and the sheath. Access to the pleural cavity is then limited to the channel 301 through the sheath 300.

The guiding section 304 is able to guide the heat exchange unit 220 in a specific direction as dictated by the orientation of the guiding section 304.

Advantageously, the sheath is L-shaped with a rounded corner. The end of the guiding section being farthest from the channel does not comprise a hard material, but is made from a flexible material ensuring that rotating the sheath does not cause excessive trauma on the cavity. To control the orientation of the guiding section after insertion, when it cannot visually be determined, the channel preferably has a mark above the fastening means to signify the orientation.

Figure 4:
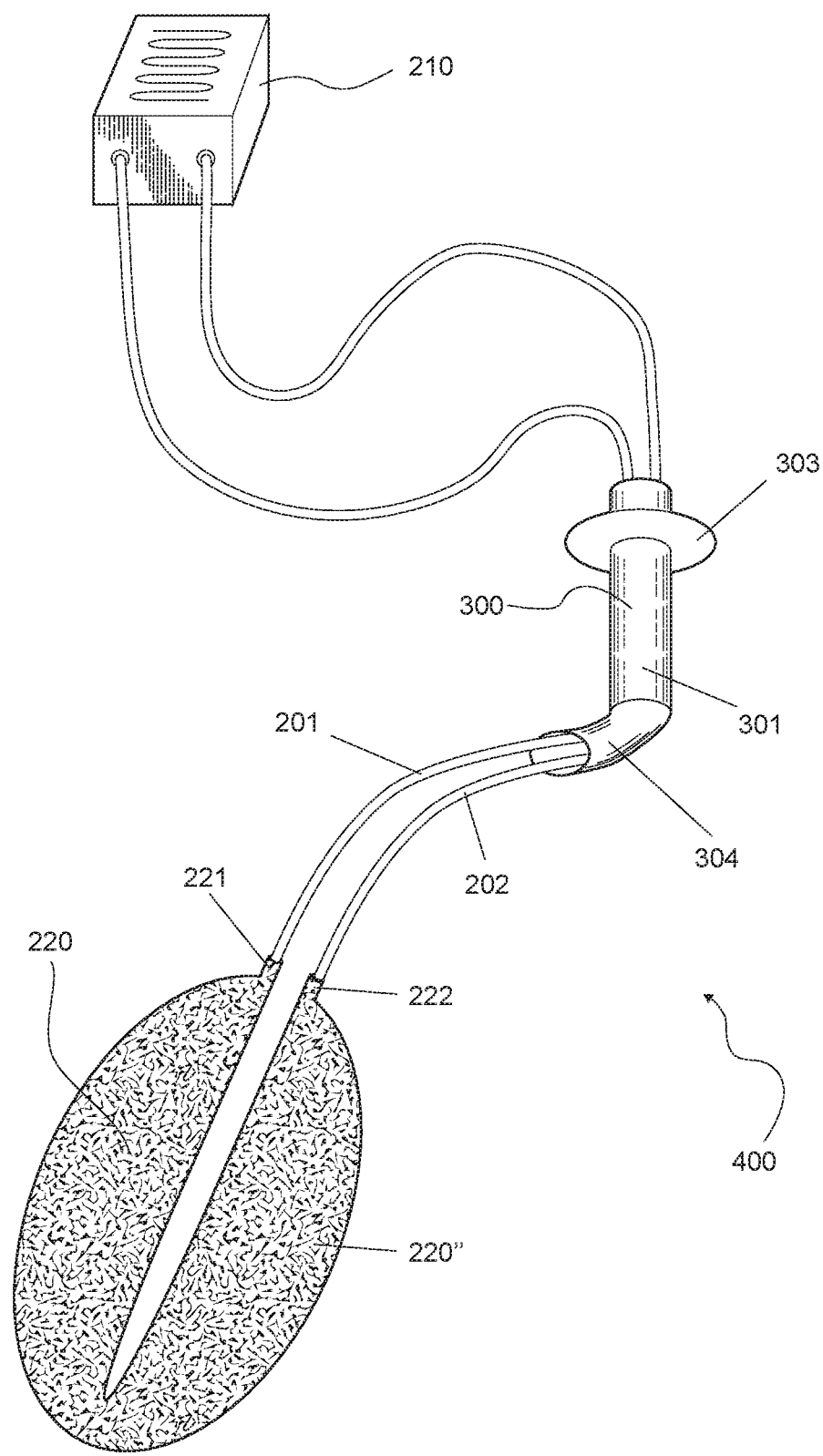

FIG. 4 illustrates the pleural heat control apparatus 400 in a position, where the heat exchange unit 220 has been inserted through the sheath 300 and then expanded by insertion of fluid.

In FIG. 4 an example embodiment of the heat exchange unit 220 is shown in the expanded state 220". The heat exchange unit 220 comprises two outer surfaces and an inner channel. The heat exchange unit may take various shapes, such as being two sheets between which the heat adjustment fluid flows, and is preferably shaped as a capillary net. By a capillary net may be understood a channel that runs from an inlet 221 to an outlet 222 through a series of channels, where these channels may be few and wide at the inlet and outlet, and thinner and more plentiful about halfway through the heat exchange unit 220. In another embodiment of the invention, capillary net signifies simply a series of channels, where these may diverge and converge in any manner throughout the inner channel. These tubes may advantageously be the inner surface of two mutually adhered sheets thus affording structural integrity to the capillary net meaning at least that the tubes do not tangle or get displaced relative to each other while retaining the heat transfer rate. In an embodiment of the invention, this is important because the heat exchange unit needs to be able to expand and contract depending on the fluid content.

In an embodiment of the invention, where the heat exchange unit is adapted to be able to take at least two different shapes, it comprises at least one, possibly two and advantageously at least three elongated and rigid elements 223 running in a direction parallel to the inlet tube and outlet tube. These elements are adapted to at least partially withstand the compression of the heat exchange element on removal of fluid thus forcing the compression to be performed substantially perpendicular to the insertion direction. This element may be any useful material, such as a thicker and/or different plastic material or an enveloped metal wire or bendable metal sheet.

In an embodiment of the invention, where the heat exchange unit is adapted to be able to take at least two different shapes, it comprises at least one elongated, substantially elastic element running perpendicular to the insertion direction of the heat exchange unit, and where this element is in a relaxed state when the heat exchange unit is compressed and is in an expanded state when the heat exchange unit is in an expanded state. On decompression, this elastic material ensures that compression is performed substantially perpendicular to the insertion direction. This element may be of any useful material, such as any rubber type material.

The heat exchange unit 220 has at least two openings being an inlet 221 and an outlet 222, where the two openings are placed at opposite ends of the fluid channel of the heat exchange unit 220. These two ends may be physically placed close to each other depending on the specific shape of the fluid channel and heat exchange unit. For example, by constructing the heat exchange unit as substantially U-shaped, the fluid channel may begin and end physically close to each other allowing both openings to enter the patient as the last part of the heat exchange unit thus allowing a single hole to hold both the inlet and outlet catheters. Other shapes may be envisioned using the same principles as mentioned here, such as substantially M-shaped, wave-shaped and even being circular or square.

In an embodiment of the invention, the heat exchange unit may not need to be U-shaped, instead only the fluid channel needs to be U-shaped.

By monitoring the fluid pressure of the inlet tube 201 and the outlet tube 202 and comparing them, a controlled expansion of the heat exchange unit may be achieved. When the heat exchange unit is compressed and inserted in the desired position, inserting heat controlling liquid through the inlet tube expands the heat exchange unit. This increases the pressure in the inlet tube, where the outlet tube may still be empty or without significant liquid pressure. In an embodiment of the invention, fluid flow is blocked in the outlet tube, whereby liquid inserted through the inlet tube necessarily expands the heat exchange unit. As the heat exchange unit expands, the resistance to this expansion produces a pressure in the inlet tube which is then measured in the treatment controller unit. When the heat exchanger unit is fully expanded, the flow increases prompting a pressure drop which is used to initiate the liquid circulation. Ideally, a tolerance should be observed ensuring that the heat exchange unit and catheters do not break due to pressure built. This can be performed manually or ideally by the treatment controller unit.

FIG. 5 is a side view of the first steps of treatment according to the invention. First, a cut is made to the desired cavity such as preferably the pleural cavity (not shown). By using the pleural cavity, a central position in the body is used, where heat exchange is performed in close proximity to heart and lungs without directly intervening in the blood flow of the body. Heart and lungs are heated which is effective since these are central to the blood circulation system, while not opening the blood circulatory system up directly avoids a series of complications. After the cut has been made, a sheath 300 is inserted into the produced hole.

The guiding section 304 is inserted first. When the length of the sheath is inside the hole, the sheath can be controllably rotated inside the hole, where rotation of the sheath rotates the guiding section 304. In an embodiment, the sheath is inserted with the guiding element pointing parallel to the length of the body and plane A as shown in FIG. 5A. Then, as seen in FIG. 5B, the sheath 300 is rotated approximately ninety degrees or another angle suitable to bring the guiding element to direct the heat transfer unit 220 towards the front centre of the body and thus substantially over the lungs and/or heart, this angle being substantially plane B. This desired orientation may vary substantially from plane B by an angle of even ninety degrees in either direction, preferably forty-five degrees or most preferably twenty-five degrees relative to plane B. By this inserting in direction A, ease of insertion is achieved. By rotating to plane B, the most effective treatment is achieved.

In an embodiment of the invention, the sheath, once inserted into the hole and rotated so the guiding element directs it in a desired angle, is then fastened to the body with fastening means 303. This ensures that the guiding element retains its correct orientation. Treatment may be momentarily paused at this point due to the self-sealing means in the sheath. Thereby, even a relatively short transportation may be used for treatment according to the invention preparing for later steps to be performed.

FIG. 6 is a side view of subsequent steps of treatment according to the invention. First, the heat exchange unit 220 is moved through the sheath 300 which has been prepared with the intended guiding angle, as seen in FIG. 6A. When the heat exchange unit has been inserted into its desired position, liquid is moved through the inlet tube 201 and into the heat exchange unit 220. As the liquid enters the heat exchange unit, it expands the channels running through it and eventually fully expands the heat exchange unit, as seen in FIG. 6B. When the heat exchange unit is fully expanded, fluid flow increases thus prompting a decrease in pressure at the inlet tube and signaling the fluid circulation to begin, and the treatment controller unit draws liquid from the outlet tube.

As the heat exchange unit and catheter are moved through the sheath, either the heat exchange unit or catheter may comprise a fluid-sealing means, such as a plug to fit inside the sheath or an adhesive surface to fasten to the area around the hole. This is especially advantageous if the self-sealing means 302 of the sheath 300 loses its sealing ability once the heat exchange unit has passed through, such as if it is a breakable membrane.

In an embodiment of the invention, the heat exchange unit is designed to have the smallest volume when inserted, but to have the maximal surface area when inserted and expanded.

After use, the heat exchange unit is compressed whereupon it is carefully extracted from the cavity through the sheath.

By this method, a conventional operating procedure of gaining access to the pleural cavity through a hole under the armpit may be used in conjunction with new steps to achieve the means of the invention, and so no or few complicated or specialised methods must be performed to treat according to the invention. Even in situations, where no specialist personnel is available, the operation may be started or completed on site or during transportation to a hospital. Inserting the sheath is a simple procedure, while inserting and activating the heat exchange unit only require the closed liquid system and relatively low volume of saline comprised in the system, which may be as little as 10 litres, 5 litres, 4 litres, 3 litres, 2 litres, 1 litre, or even 0.5 litres.

Further, in an embodiment of the invention, two parallel heat exchange systems may be inserted, one into each of the two pleural cavities of a patient to work simultaneously. In another embodiment, any number of heat exchange units may be used simultaneously. In the art, by direct injection of saline, one pleural cavity is filled with saline, while the other is drained. Thus, the invention further achieves a significantly higher and/or more controlled heat transfer rate.

In an embodiment of the invention, the heat exchange unit is merely inserted partway through the sheath.

The heat exchange unit 220 is illustrated in FIG. 7A as an expanded heat exchange unit 220". In this state, the heat exchange unit is full of fluid. From this state, the heat exchange unit is emptied of fluid, thus being prepared for insertion into the patient. The heat exchange unit is a channel through which liquid flows to transfer heat between the liquid and the body.

The heat exchange unit is formed from a flexible material which allows it to be compressed before insertion into the body and then being expandable after insertion. This compression may be performed in a variety of ways, where bending it in a wave-like fashion such as in FIG. 8 may be advantageous to allow easy expansion by introduction of liquid in its inner channel after insertion. The heat exchange unit is compressed either before connection to the liquid system 200, such as at time of production, or it is compressed by the treatment controller. In an embodiment of the invention, the heat exchange unit compresses automatically. In this state, the outer diameter of the heat exchange unit is smaller than the inner diameter of the sheath, and it may thus be inserted through the sheath 300. In another embodiment of the invention, the compression of the heat exchange unit 220 is enhanced by inserting it into a tube having a fitting diameter during compression, where a fitting diameter may be a diameter equal to the diameter of the sheath.

The heat exchange unit 220 is produced in a flexible medical grade material, such as silicone, polyurethane, polyethylene, polytetrafluoroethylene or another material, typically a polymer and has at least two openings being an inlet 221 and an outlet 222, as seen illustrated in FIGS. 7B and 7C.

FIG. 7C illustrates yet another embodiment comprising only one elongated, substantially elastic element running perpendicular to the insertion direction of the heat exchange unit.

Figure 8:
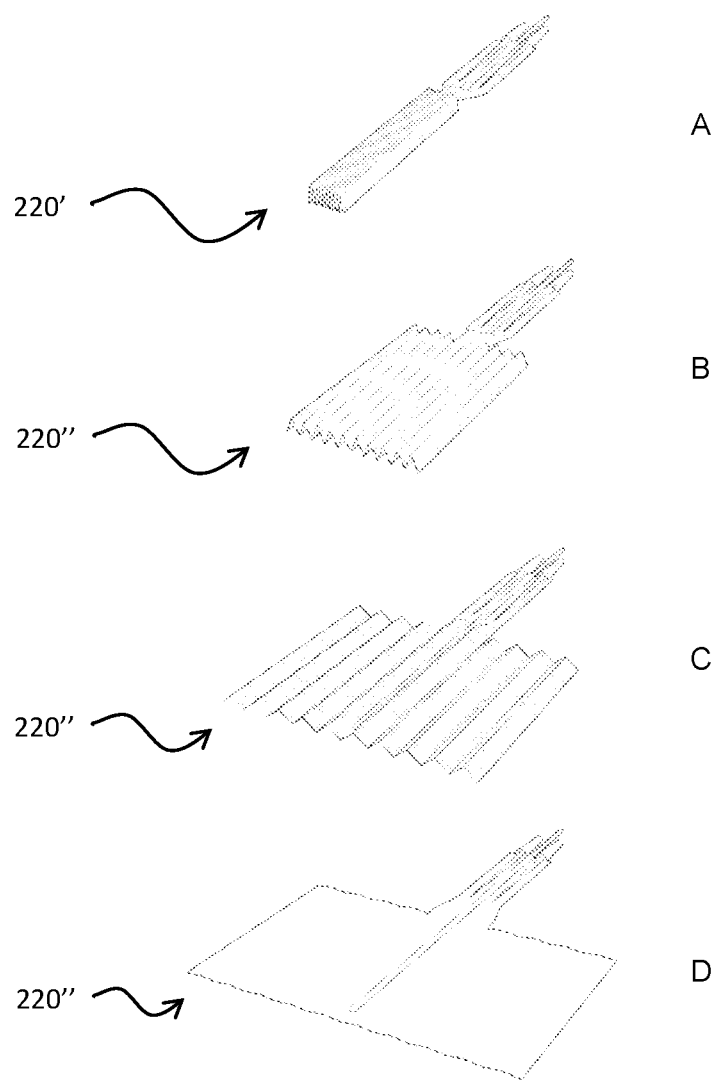

FIG. 8 shows the sequential unfolding of a heat exchange unit 220 from a compressed state 220' to an expanded state 220".

REFERENCE NUMBERS

101—preferred insertion area
200—liquid heat transfer system
201—inlet tube
202—outlet tube
210—treatment controlling device
220—heat exchange unit
220'—compressed heat exchange unit
220"—expanded heat exchange unit
221—inlet
222—outlet
223—elongated element
300—sheath
301—channel
302—self-sealing means
303—fastening means
304—guiding section
400—pleural heating apparatus
A—preferred insertion direction
B—preferred guiding direction

The invention claimed is:

1. A system for adjusting a temperature of a body comprising:
a sheath (300) for providing a channel (301) from outside said body to a pleural cavity inside said body, said channel (301) being configured to allow passage of a non-intravenous heat exchange unit (220) for heating or cooling said pleural cavity;
wherein said sheath comprises a guiding section (304) being angular to said channel (301)
the non-intravenous heat exchange unit (220) comprising an inner fluid channel, an outer contour, a fluid inlet (221), and a fluid outlet (222), where at least a part of said inner fluid channel of said heat exchange unit (220) is adapted for passing liquid through said fluid inlet (221) into and through said inner fluid channel and from said inner fluid channel through said fluid outlet (222), and
wherein said heat exchange unit is adapted to change shape, wherein a compressed shape is achieved where the outer contour of said heat exchange unit (220) is smaller than the inner diameter of said channel (301) of said sheath (300) and the inner diameter of said guiding section (304) of said sheath (300) and
wherein the compressed shape is further achieved by the heat exchange unit being folded in a wave-like manner; and
wherein said at least part of said inner fluid channel of said heat exchange unit is adapted for inserting through the channel (301) of said sheath (300) and into said pleural cavity inside a body in a compressed state, and where liquid entering the fluid inlet (221) and into the heat exchange unit (220) expands the inner fluid channel and eventually expands the heat exchange unit (220); and at least one elongated and rigid element running in a direction parallel to the fluid inlet and the fluid outlet adapted to at least partially withstand the compression of the heat exchange element on removal of fluid thus forcing the compression to be performed substantially perpendicular to the insertion direction.

2. The system according to claim 1, where said guiding section (304) is rotatable around an axis extending through the channel by rotating said channel (301).

3. The system according to claim 1, wherein the angle of the guiding section (304) is substantially perpendicular relative to the channel (301).

4. The system according to claim 1, wherein said sheath (300) further comprises fastening means (303) for securing said sheath (300) to the body.

5. The system according to claim 1, wherein said sheath (300) further comprises a self-sealing means (302) inside said channel (301).

6. The system according to claim 5, where the self-sealing means (302) comprises a compressible, at least partially fluid-impregnable sponge.

7. The system according to claim 5, where the self-sealing means (302) comprises the walls of said channel being flexible allowing said walls to collapse under the pressure of displaced tissue.

8. The system according to claim 1 further comprising a treatment controlling means (210) for modifying a temperature of a liquid passing through said treatment controlling means (210).

9. The system according to claim 8, wherein said system further comprises an inlet tube (201) for passing liquid from said treatment controlling means (210) to said fluid inlet (221) of said heat exchange unit (220) and an outlet tube (102) for passing liquid from said fluid outlet of said heat exchange unit (220) to said treatment controlling means (210).

10. A non-intravenous heat exchange unit (220) for a system for adjusting a temperature of a body comprising:

an inner fluid channel;

an outer contour;

a fluid inlet (221); and a fluid outlet (222), wherein at least a part of said inner fluid channel is adapted for passing liquid through said fluid inlet (221) into and through said inner fluid channel and from said inner fluid channel through said fluid outlet (222), wherein said heat exchange unit is adapted to change shape, wherein a compressed shape is achieved where the outer contour of said heat exchange unit (220) is smaller than an inner diameter of a channel (301) of a sheath (300) and an inner diameter of a guiding section (304) of said sheath (300), wherein the compressed shape is further achieved by the heat exchange unit being folded in a wave-like manner; and wherein said at least part of said inner fluid channel of said heat exchange unit is adapted for inserting through said channel (301) of said sheath (300) and into said pleural cavity inside a body in a compressed state, and where liquid entering the fluid inlet (221) and into the heat exchange unit (220) expands the inner fluid channel and eventually expands the heat exchange unit (220); and at least one elongated and rigid element running in a direction parallel to the fluid inlet and fluid outlet adapted to at least partially withstand the compression of the heat exchange element on removal of fluid thus forcing the compression to be performed substantially perpendicular to the insertion direction.

\* \* \* \* \*